United States Patent [19]

Nakamura et al.

[11] Patent Number: 4,595,701

[45] Date of Patent: Jun. 17, 1986

[54] PROCESS FOR PRODUCING ALIPHATIC ALCOHOLS

[75] Inventors: Shuzo Nakamura, Takatsuki; Takashi Deguchi, Kusatsu; Mitsuhisa Tamura, Ibaraki; Masaru Ishino, Takatsuki; Keisuke Wada, Yokohama; Eiichi Watanabe, Shiroyama; Yoshinori Hara; Kenji Murayama, both of Machida; Hiroo Tanaka, Yokohama, all of Japan

[73] Assignee: Agency of Industrial Science and Technology, Tokyo, Japan

[21] Appl. No.: 685,893

[22] Filed: Dec. 24, 1984

[30] Foreign Application Priority Data

Dec. 26, 1983 [JP] Japan .................................. 58-244171
Jan. 10, 1984 [JP] Japan .................................... 59-1408
Jan. 17, 1984 [JP] Japan .................................... 59-4750
Nov. 2, 1984 [JP] Japan ................................ 59-230235

[51] Int. Cl.$^4$ .............................................. L07C 27/06
[52] U.S. Cl. .................................... 518/701; 518/700; 502/155; 502/162
[58] Field of Search ................................ 518/700, 701

[56] References Cited

U.S. PATENT DOCUMENTS

| 3,989,799 | 11/1976 | Brown | 518/700 |
| 4,315,993 | 2/1982 | Knifton | 518/700 |
| 4,315,994 | 2/1982 | Knifton | 518/701 |
| 4,391,919 | 7/1983 | Burdett | 518/701 |
| 4,421,862 | 12/1983 | Bradley | 518/700 |
| 4,460,709 | 7/1984 | Kiso et al. | 518/700 |

FOREIGN PATENT DOCUMENTS 75937 4/1983 European Pat. Off. ............ 518/701

Primary Examiner—Howard T. Mars
Attorney, Agent, or Firm—Oblon, Fisher, Spivak, McClelland & Maier

[57] ABSTRACT

A process for producing aliphatic alcohols by reacting carbon monoxide and hydrogen in a liquid phase in the presence of catalyst components, characterized in that rhodium and a trialkylphosphine represented by the general formula $PR_1R_2R_3$ where each of $R_1$, $R_2$ and $R_3$ is a primary alkyl group, a secondary alkyl group, a tertiary alkyl group or a cycloalkyl group, are used as the catalyst components.

15 Claims, No Drawings

PROCESS FOR PRODUCING ALIPHATIC ALCOHOLS

The present invention relates to a process for producing aliphatic alcohols by reacting carbon monoxide and hydrogen in a liquid phase. More particularly, the present invention relates to a process for producing lower aliphatic alcohols, particularly ethylene glycol and methanol, directly from a mixture of carbon monoxide and hydrogen (hereinafter referred to simply as "synthesis gas") in a liquid phase.

Ethylene glycol is an industrially important chemical substance useful as a starting material for polyester fibers and organic solvents or as a non-volatile anti-freezing agent. At present, it is usually prepared from ethylene as the starting material, by subjecting ethylene to an oxidation reaction and a hydration reaction. On the other hand, methanol is an important basic chemical substance which is widely used as a raw material for formalin, acetic acid, dimethyl phthalate or methacrylic acid or as a solvent, and is usually prepared by reacting the synthesis gas in a gas phase under a high temperature high pressure condition.

In recent years, there have been proposed various methods for producing lower aliphatic alcohols in a liquid phase directly from synthesis gas as the starting material. In these methods, it is known to use a catalyst containing rhodium or a catalyst containing ruthenium.

For the use of a catalyst containing rhodium, there have been proposed a number of methods. For instance, Japanese Unexamined Patent Publications Nos. 36403/1976, 32506/1976 and 63110/1976, disclose that an addition of an alkali metal salt, a quaternary ammonium salt or a bis(tertiary phosphine) iminium salt as a cocatalyst is effective. Further, Japanese Unexamined Patent Publications Nos. 68509/1973, 42809/1977 and 42810/1977 disclose an addition of an organic nitrogen ligand or an organic oxygen ligand. Furthermore, Japanese Unexamined Patent Publication No. 9065/1980 discloses the use of a phosphine oxide as a co-catalyst.

As other references which disclose the use of rhodium as a catalyst, there may be mentioned Japanese Unexamined Patent Publications Nos. 32117/1975, 32118/1975, 32507/1976, 88902/1976, 125203/1976, 42808/1977, 108889/1978, 121714/1978, 124204/1978, 16415/1979, 48703/1979, 71098/1979, 92903/1979, 122211/1979, 75498/1981, 128645/1982, 130941/1982 and 130942/1982, Japanese Examined Patent Publication No. 43821/1980, and U.S. Pat. Nos. 4,013,700, 4,199,520, 4,133,776, 4,151,192, 4,153,623, 4,225,530, 4,199,521, 4,190,598, 4,302,547 and 4,211,719. However, none of these methods is fully satisfactory with respect to the catalytic activity and selectivity, or it is thereby difficult to recycle the catalyst for reuse. For these reasons, these methods have not yet been industrially employed.

Catalysts containing ruthenium are disclosed in e.g. Japanese Unexamined Patent Publications Nos. 115834/1980, 100728/1981, 51426/1981, 109735/1982, 123128/1982, 130937/1982 and 130939/1982. These catalysts are also inadequate in catalytic activity, and their selectivity for ethylene glycol is at a low level.

Further, a method for carrying out the reaction in the presence of both rhodium and ruthenium, is disclosed in e.g. Japanese Unexamined Patent Publications Nos. 123925/1981, 128644/1982, 123128/1982, 118527/1983, 118528/1983 and 121227/1983. These catalysts are also inadequate in their catalytic activity, and their selectivity for ethylene glycol is at a low level.

Thus, in the prior art processes mentioned above, the catalytic activity which justifies the use of expensive rhodium has not yet been realized, and none of them is qualified as a process employable in an industrial scale.

Under these circumstances, the present inventors have conducted extensive research with an aim to overcome the difficulties of the conventional catalysts, and have finally found that by using rhodium and a trialkyl phosphine as catalyst components, the activity for the production of lower aliphatic alcohols can be remarkably improved, and the yield of ethylene glycol can substantially be increased, and that the coexistence of an amine compound is further effective. More surprisingly, it has been found that by using a trialkylphosphine in the presence of both rhodium and ruthenium, the activity for the production of lower aliphatic alcohols can further be improved, and that the coexistence of an amine compound is effective also in this case. The present invention has been accomplished based on these discoveries.

The object of the present invention is to provide a process for industrially advantageously producing aliphatic alcohols such as ethylene glycol and methanol, which are industrially important chemical substances.

In the broadest sense, the present invention provides a process for producing aliphatic alcohols by reacting carbon monoxide and hydrogen in a liquid phase in the presence of catalyst components, characterized in that rhodium and a trialkylphosphine represented by the general formula $PR_1R_2R_3$ where each of $R_1$, $R_2$ and $R_3$ is a primary alkyl group, a secondary alkyl group, a tertiary alkyl group or a cycloalkyl group, are used as the catalyst components.

Now, the present invention will be described in detail with reference to the preferred embodiments.

In the present invention, the presence of rhodium as a catalytic component is essential. The rhodium component may be supplied in the form of rhodium metal or a rhodium compound which is capable of forming a rhodium carbonyl compound in the reaction zone.

As specific examples of such rhodium compounds, there may be mentioned a zero valence compound such as dirhodium octacarbonyl; a monovalent complex compound such as acetylacetonatobis(carbonyl)-rhodium or bromotris(pyridine)rhodium; a salt such as rhodium trichloride, rhodium nitrate, rhodium formate, rhodium acetate, rhodium (II) propionate, rhodium (II) butyrate, rhodium (II) valerate or rhodium (II) naphthenate; an oxide such as rhodium oxide or rhodium trihydroxide; a trivalent complex compound such as tris(acetylacetonato) rhodium; a cluster such as tetrarhodium dodecacarbonyl or hexarhodium hexadecacarbonyl; and an anion complex such as rhodium tetracarbonyl-anion or carbidohexarhodium pentadecacarbonyl-dianion.

Further, it is also possible to use a rhodium compound to which a trialkylphosphine having a function to facilitate the reaction as a catalyst component, as will be described hereinafter, is coordinated beforehand. As specific examples, there may be mentioned $RhH[P(i-Pr)_3]_3$, $RhH(PEt_3)_4$, $RhH(PEt_3)_3$, (trans-$Rh(CO)(py)$ [$P(i-Pr)BPh_4$, trans-$RhH(CO)[P(c-C_6H_{11})_3]_2$, trans-$RhH(CO)[P(i-Pr)_3]_2]_2$, $Rh(CO)[P(n-Bu)_3]_2$, $RhH[P(t-Bu)_3]_2$, $RhH[P(c-C_6H_{11})_3]_2$, $[Rh(CO)_3P(i-Pr)_3]_2$, $Rh_2(CO)_3[P(i-Pr)_3]_3$, $Rh_2(CO)_4[P(t-Bu)_3]_2$ and $Rh_2(CO)_4[P(c-C_6H_{11})_3]_2$. (In the above chemical formulas, i-Pr is an isopropyl group, Et is an ethyl group, py is pyridine, Ph is a phenyl group, c-$C_6H_{11}$ is a cyclohexyl group, n-Bu is a n-butyl group, and t-Bu is a t-butyl group.)

The concentration of rhodium in the reaction solution is usually within a range of from 0.0001 to 10 g atom, preferbly from 0.001 to 10 g atom, more preferably from 0.001 to 1 g atom, as rhodium atom, per 1 liter of the reaction solution.

In the process of the present invention, it is effective to use ruthenium as a catalyst component in combination with rhodium. The ruthenium component may be supplied in the form of ruthenium metal or a ruthenium compound capable of forming a ruthenium carbonyl compound in the reaction zone.

As specific examples of such a ruthenium compound, there may be mentioned a salt such as ruthenium (III) chloride, ruthenium (III) bromide, ruthenium (III) nitrate or ruthenium (III) acetate; an oxide such as ruthenium (IV) oxide; a complex compound such as tris-(acetylacetonato)ruthenium, dicarbonyl(methyl)(cyclopentadienyl)ruthenium, dicarbonyl-bis(allyl)ruthenium, dichlorotricarbonylruthenium dimer or ruthenocene; and a cluster such as tetrahydridotetraruthenium dodecacarbonyl or triruthenium dodecacarbonyl. In the case where ruthenium is used in combination with rhodium, the amount of ruthenium is related to the amount of rhodium. Namely, the sum of the amounts of rhodium and ruthenium as metals should be within the above-mentioned range for the amount of rhodium. Namely, the total concentration of rhodium and ruthenium as metals in the reaction solution is usually within a range of from 0.0001 to 10 g atom, preferably from 0.001 to 10 g atom, more preferably from 0.001 to 1 g atom, per 1 liter of the reaction solution.

The ratio of the rhodium component to the ruthenium component is not critical and is not particularly limited. However, the atomic ratio of ruthenium to the sum of ruthenium and rhodium as metals (Ru/Ru+Rh) is preferably from 0.1 to 0.9. The use of ruthenium serves to stabilize the catalyst and to prevent the loss of expensive rhodium.

In the present invention, it is essential to use a trialkylphosphine having a function to facilitate the reaction, as a catalyst component.

The trialkylphosphine is believed to be coordinated to rhodium as the main catalyst and have a function to control the electronic state. The mechanism of the control is not clearly understood. However, it is believed that the ability of the trialkylphosphine as an electron donor plays an important role. In fact, the hydrogenation activity of the rhodium-phosphine catalyst system and the selectivity for ethylene glycol in the reaction intended by the present invention, substantially vary depending upon the type of the phosphine. Accordingly, in order to attain a high level of the ethylene glycol yield, it is particularly effective to employ, among various phosphines, a trialkylphosphine represented by the general formula $PR_1R_2R_3$ where each of $R_1$, $R_2$ and $R_3$ is a primary alkyl group, a secondary alkyl group, a tertiary alkyl group or a cycloalkyl group, and they may be the same or different from one another. In this case, it is believed that the electronic interaction among the alkyl groups in the trialkylphosphine molecule serves to adjust the physical constant for the above-mentioned ability as the electron donor to a desirable state, whereby a favorable property as the accelerator is brought about.

Further, by using such a phosphine, it is possible to improve the stability of the catalyst and to prevent the formation of metallic precipitation which used to be a serious problem when a rhodium catalyst was used.

As specific examples of the trialkylphosphine which may be used in the present invention, there may be mentioned a trialkylphosphine having three primary alkyl groups, such as trimethylphosphine, triethylphosphine, tri-n-propylphosphine, tri-n-butylphosphine, tri-n-hexylphosphine, tri-n-octylphosphine, tri-iso-butylphosphine, tris(2-ethylhexyl)phosphine or di-n-butyl-iso-butylphosphine; a trialkylphosphine having three secondary alkyl, tertiary alkyl or cycloalkyl groups (hereinafter referred to generally as "α-branched alkyl groups"), such as tri-iso-propylphosphine, tri-sec-butylphosphine, tri-t-butylphosphine, tricyclopentylphosphine, tricyclohexylphosphine, tri-t-amylphosphine, tris(dimethylisopropyl)phosphine, tris(pentamethylethyl)phosphine, di-iso-propyl-cyclopentylphosphine, di-isopropyl-sec-butylphosphine, di-iso-propyl-t-butylphosphine, di-t-butyl-iso-propylphosphine, di-t-butyl-sec-butylphosphine, di-sec-butyl-iso-propylphosphine, di-sec-butyl-t-butylphosphine, di-iso-propyl-cyclohexylphosphine, di-t-butyl-cyclopentylphosphine, di-t-buty-cyclohexylphosphine, di-sec-butyl-cyclohexylphosphine, dicyclopentyl-iso-propylphosphine, dicyclopentyl-t-butylphosphine, dicyclohexyl-iso-propylphosphine, dicyclohexyl-t-butylphosphine, dicyclohexyl-sec-butylphosphine, diadamantyl-iso-propylphosphine, cyclopentyl-cyclohexyl-t-butylphosphine, tris(1-bicyclo[2,2,2]octyl)phosphine or tris(1-bicyclo[2,2,1]heptyl)phosphine; a trialkylphosphine having two primary alkyl groups and one α-branched alkyl group, such as iso-propyl-diethylphosphine, iso-propyl-di-n-butylphosphine, iso-propylethyl-n-butylphosphine, t-butyl-diethylphosphine, t-butyl-di-n-propylphosphine, t-butyl-di-n-butyl phosphine, cyclopentyl-diethylphosphine, di-n-butyl cyclopentylphosphine, cyclopentyl-di-n-propylphosphine, cyclopentyl-ethyl-n-butylphosphine, cyclohexyl-diethylphosphine, cyclohexyl-di-n-octylphosphine, adamantyldiethylphosphine, adamantyl-di-n-butylphosphine, norbornyl-diethylphosphine or norbornyl-di-n-butylphosphine; and a trialkylphosphine having one primary alkyl group and two α-branched alkyl groups, such as di-iso-propyl-ethylphosphine, di-iso-propyl-n-butylphosphine, di-t-butyl-methylphosphine, di-t-butyl-ethylphosphine, di-t-butyl-n-propylphosphine, di-t-butyl-n-butylphosphine, dicyclopentylethylphosphine, dicyclopentyl-n-propylphosphine, dicyclopentyl-n-butylphosphine, dicyclohexyl-methylphosphine, dicyclohexylethylphosphine, dicyclohexyl-n-butylphosphine, dicyclohexyl-n-propylphosphine, diadamantyl-ethylphosphine, diadamantyl-n-butylphosphine, dinorbornylethylphosphine, dinorbornyl-n-butylphosphine, iso-propyl-t-butyl-n-butylphosphine, t-butyl-cyclohexylethylphosphine or iso-propyl-cyclopentyl-n-octyl-phosphine.

Among the above-mentioned phosphines, a suitable trialkylphosphine varies depending upon many factors of the catalyst system employed, such as the type and amount of the metal components (rhodium and, if applicable, ruthenium) or the type and amount of the amine compound. In practice, a suitable trialkylphosphine is selected by experiments.

Among the above trialkylphosphines, those having both primary alkyl and α-branched alkyl groups, i.e. trialkylphosphines represented by the general formula $PR_1R_2R_3$ where $R_1$ is a primary alkyl group, $R_2$ is a secondary alkyl group, a tertiary alkyl group or a cycloalkyl group, and $R_3$ is a primary alkyl group, a secondary alkyl group, a tertiary alkyl group or a cycloalkyl group, include many trialkylphosphines having delicately different characteristics, and in the practical selection of a suitable trialkylphosphine, it is advantageous to select a suitable phosphine from such trialkylphosphines.

As parameters with which the function of the phosphine compound as a ligand to control the electronic state of metal is explained, C. A. Tolman has proposed a parameter $\theta$ (unit: deg) for a steric factor and a parameter $\nu$ (unit: $cm^{-1}$) for an electronic factor, in Chemical Reviews (1977), Vol. 77, No. 3, pages 313–348. Further, T. T. Derencsenyi has proposed a chemical shift value $\delta$(ppm) of $^{31}$P-nmr of the corresponding phosphine oxide as a parameter relating to the basicity of the phosphine compound and the reaction rate in a uniform complex reaction, in Inorganic Chemistry (1981), Vol. 20, No. 3, pages 665–670.

The trialkylphosphines to be used in the present invention may be represented by $\theta$, $\nu$ and $\delta$, as follows: usually $\theta$(115–190 deg), $\nu$(2050–2080 $cm^{-1}$), $\delta$(−80 –0 ppm), preferably $\theta$(140–185 deg), $\nu$(2055–2070 $cm^{-1}$), $\delta$(−75––30 ppm), more preferably $\theta$(150–185 deg), $\nu$(2055–2060 $cm^{-1}$), $\delta$(−70––40 ppm).

These trialkylphosphines are usually employed in an amount within a range of at least 0.2 mol, preferably from 0.2 to 1000 mols, more preferably from 0.2 to 500 mols, further preferably from 0.5 to 100 mols, relative to 1 g atom of rhodium. Particularly preferred is a range of from 0.8 to 10 mols. Further, in the case where a ruthenium component is used in combination with the rhodium component, the trialkylphosphines are employed in an amount within a range of at least 0.2 mol, preferably from 0.2 to 1000 mols, more preferably from 0.2 to 500 mols, further preferably from 0.5 to 100 mols, particularly preferably from 0.8 to 10 mols, relative to 1 g atom of the total of rhodium and ruthenium as metals.

In the process of the present invention, the activity of the catalyst can remarkably be improved by using an amine compound in combination with the trialkylphosphine.

The function of the amine compound is not clearly understood. However, it appears that the amine compound plays a role as a ligand or a role of presenting a counter cation to stabilize an anionic rhodium compound or an anionic ruthenium compound formed in the reaction system. In the present invention, various amine compounds may be used.

As specific examples of the amine compound which may be used in the present invention, there may be mentioned an inorganic amine such as ammonia, hydroxylamine or hydrazine; an aliphatic amine such as methylamine, ethylamine, n-propylamine, isopropylamine, octylamine, dimethylamine, diethylamine, di-n-propylamine, methylethylamine, trimethylamine, triethylamine, triisopropylamine, triisobutylamine or tridecylamine; an alicyclicamine such as cyclohexylamine, dicyclohexylamine, tricyclohexylamine or dicyclohexylmethylamine; an ethyleneimine such as ethyleneimine or methylethyleneimine; a pyrrolidine such as pyrrolidine or 1-methylpyrrolidine; a pyrrole such as pyrrole; a piperidine such as piperidine, 1-methylpiperidine, 2-methylpiperidine, 3-methylpiperidine or 4-ethylpiperidine; a pyridine such as pyridine, 2-methylpyridine, 3-methylpyridine, 4-ethylpyridine, 2,4,6-trimethylpyridine, 4-aminopyridine, 2-aminopyridine, 2-dimethylaminopyridine, 2-methylaminopyridine, 4-anilinopyridine, 4-methylaminopyridine, 4-dimethylaminopyridine or 2,2'-dipyridyl; a quinoline such as quinoline, 2-(dimethylamino)quinoline or 4-(dimethylamino)quinoline; a phenanthroline such as 4,5-phenanthroline or 1,8-phenanthroline; a piperazine such as piperazine, 1-methylpiperazine or 1-phenylpiperazine; a cyclic amine such as diazabicycloundecene or diazabicyclooctane; an imidazole such as imidazole, 1-methylimidazole, 2-methylimidazole, 1-ethylimidazole, 1,2-dimethylimidazole, 1,5,6-trimethylimidazole, benzimidazole, 1-methylbenzimidazole, 1-ethylbenzimidazole, 5,6-dimethylbenzimidazole, 1,5,6-trimethylbenzimidazole or 2-methylbenzimidazole; a polyazole such as triazole, 1-benzyltriazole, 1-methyltriazole, benzotriazole, 1-methylbenzotriazole, 1-ethylbenzotriazole, 2-methylbenzotriazole, 5,6-dimethylbenzotriazole, tetrazole or 1-methyltetrazole; an aromatic amine such as aniline, 1-naphthylamine, 2-naphthylamine, o-toluidine, p-toluidine, o-3-xylidine, benzylamine, diphenylamine, dimethylaniline, diethylaniline, 1,8-diaminonaphthalene or 1,8-bis(dimethylamino)naphthalene; an aliphatic or aromatic polyamine such as 1,2-ethanediamine, 1,3-propanediamine, N,N,N',N'-tetramethylethylenediamine, N,N,N',N'-tetraethylethylenediamine, tetrakis(dimethylamino)ethylene, tetrakis(piperidino)ethylene, tetrakis(morpholino)ethylene, tetramethyl-$\Delta^{2,2'}$-bis(imidazolidine), tetrabenzyl-$\Delta^{2,2'}$-bis(imidazolidine), o-phenylenediamine, p-phenylenediamine or N,N,N',N'-tetramethyl-p-phenylene diamine; and an oxygen-containing amine such as ethanolamine, diethanolamine, morpholine, methylmorpholine, 2-hydroxypyridine, 2-methoxypyridine, 4-hydroxypyridine, 4-methoxypyridine, 4-phenoxypyridine, 2-methoxyquinoline, 2-hydroxyimidazole or 2-methoxybenzimidazole. Among the above-mentioned amines, organic amines are preferred.

The amount of the amine compound may vary depending upon the particular case. However, the amine compound is used usually in an amount within a range of from 0.001 to 1000 mols, preferably from 0.1 to 500 mols, more preferably from 1 to 100 mols, relative to 1 g atom of rhodium. Further, in the case where a ruthenium component is used in combination with the rhodium component, it is used usually in an amount within a range of from 0.001 to 1000 mols, preferably from 0.1 to 500 mols, further preferably from 1 to 100 mols, relative to 1 g atom of the total of rhodium and ruthenium as metals. However, when the amine compound is used as a solvent as will be described hereinafter, the amount of the amine compound is not necessarily limited within the above range.

The reaction of the present invention is conducted in a liquid phase. It may be conducted in the absence of a solvent, i.e. by using the starting materials for the reaction and the catalyst components as the solvent. However, it is preferred to conduct the reaction in the presence of a solvent.

As such a solvent, there may be mentioned an ether such as diethyl ether, anisole, tetrahydrofuran, ethylene glycol dimethyl ether or dioxane; a ketone such as acetone, methyl ethyl ketone or acetophenone; an alcohol such as methanol, ethanol, n-butanol, benzylalcohol, phenol, ethylene glycol or diethylene glycol; a carboxylic acid such as formic acid, acetic acid, propionic acid or toluic acid; an ester such as methyl acetate, n-butyl acetate or benzyl benzoate; an aromatic hydrocarbon such as benzene, toluene, ethylbenzene or tetralin; an aliphatic hydrocarbon such as n-hexane, n-octane or cyclohexane; a halogenated hydrocarbon such as dichloromethane, trichloroethane or chlorobenzene; a nitro compound such as nitromethane or nitrobenzene; a tertiary amine such as triethylamine, tri-n-butylamine, benzyldimethylamine, pyridine, α-picoline or 2-hydroxypyridine; a carboxylic acid amide such as N,N-dimethylformamide, N,N-dimethylacetamide or N-methylpyrrolidinone; an inorganic acid amide such as hexamethylphosphoric acid triamide or N,N,N',N'-tetraethylsulfamide; a urea such as N,N'-dimethylimidazolidinone or N,N,N',N'-tetramethylurea; a sulfone such as dimethyl sulfone or tetramethylene sulfone; a sulfoxide such as dimethyl sulfoxide or diphenyl sulfoxide; a lactone such γ-butyrolactone or ε-caprolactone; a polyether such as tetraglyme or 18-crown-6; a nitrile such as acetonitrile or benzonitrile; and a carbonate such as dimethyl carbonate or ethylene carbonate.

Among the above solvent, it is preferred to use an aprotic polar solvent, such as an amine, an amide, a urea, a sulfone, a sulfoxide, a lactone, a polyether, a nitrile or a carbonate. Particularly preferred is an aprotic polar solvent having a dielectric constant of at least 20. Among the above solvents, the amine is also a catalyst component.

The starting material gases used in the present invention, i.e. carbon monoxide and hydrogen, are not particularly restricted, and they may contain a certain amount of an inert gas such as nitrogen gas, carbon dioxide or methane. The volume ratio of hydrogen to carbon monoxide is usually within a range of from 1/10 to 10/1, preferably from 1/5 to 5/1.

The reaction of the present invention may be conducted in either a homogeneous system or a heterogeneous suspension system.

The reaction temperature is usually from 100° to 350° C., preferably from 100° to 300° C., more preferably from 150° to 300° C.

The reaction pressure is usually within a range of from 100 to 3000 kg/cm², preferably from 150 to 1000 kg/cm², more preferably from 150 to 600 kg/cm², as a total of the carbon monoxide partial pressure and the hydrogen partial pressure.

The process of the present invention may be conducted in any one of the reaction systems of continuous, semicontinuous and batch systems.

The products such as ethylene glycol and methanol, may readily be separated from the reaction solution by a conventional separation operation (e.g. distillation, extraction, etc.). The catalyst remaining in the solution after the separation of the products may be recycled to the reaction system after subjecting it to various regeneration treatments or without any special treatment.

Among the conventional reactions wherein rhodium catalysts are employed, those reported to give good results include the processes disclosed in the above-mentioned Japanese Unexamined Patent Publication No. 42808/1977 and U.S. Pat. No. 4,199,520. However, the data disclosed in these prior art references are those obtained under a high pressure condition at a level of at least 1000 kg/cm², and the space time yield of ethylene glycol is reported to be at a level of about 150 g/l. hr. Likewise, according to Japanese Unexamined Patent Publication No. 121714/1978, the space time yield under the condition of 560 kg/cm² is 23.4 g/l. hr (Example 17) at best. Whereas, according to present invention, under the pressure condition at a level of 500 kg/cm², the space time yield can be as high as at least 150 g/l. hr or, in certain cases, can be improved to a level of at least 200 g/l. hr. Thus, the process of the present invention can be regarded as a process remarkably improved over the conventional processes.

Now, the present invention will be described in further detail with reference to Examples. However, it should be undestood that the present invention is by no means restricted by these specific Examples.

In the Examples, the following abbreviations were used.

EG: Ethylene glycol
MeOH: Methanol
DMI: -dimethylimidazolidinone(1,3-dimethyl-2-imidazolidinone)
NMP: N-methylpyrrolidinone(1-methyl-2-pyrrolidinone)
GBL: γ-Butyrolactone
Et: Ethyl group
n-Pr: n-Propyl group
i-Pr: Isopropyl group
n-Bu: n-Butyl group
i-Bu: Isobutyl group
s-Bu: sec-Butyl group
t-Bu: tert-Butyl group
c-$C_5H_9$: Cyclopentyl group
c-$C_6H_{11}$: Cyclohexyl group In the Examples, the space time yield represents the rate of formation of ethylene glycol based on the feed solution, and its unit is g/l. hr.

Further, in the Examples, the amount of each product is represented by a turn-over of the product in mol per 1 g atom of rhodium and per 1 hour.

EXAMPLE 1

The interior of a Hastelloy C autoclave having an internal capacity of 30 ml, was flushed with nitrogen, and then 0.025 mmol of tetrarhodium-dodecacarbonyl [$Rh_4(CO)_{12}$], 0.1 mmol of triisopropylphosphine (P/Rh=1.0) and 7.5 ml of N-methylpyrrolidinone as a solvent, were fed. Then, the gas mixture of equal volumes of carbon monoxide and hydrogen was introduced to a pressure of 350 kg/cm² at room temperature. The autoclave was heated to 240° C., and the reaction was conducted at the same temperature for 1 hour. The reaction pressure was 500 kg/cm². After the completion of the reaction, the autoclave was cooled to room temperature, the pressure was brought to normal pressure by slowly releasing the major portion of the gas. Then, the reaction mixture was taken out. The products were analyzed by gas chromatography, whereby it was found that the turn-over of EG was 21.2 mol/g atom Rh.hr and that of MeOH was 18.6 mol/g atom Rh.hr.

COMPARATIVE EXAMPLE 1

The experiment was conducted in the same manner as in Example 1 except that no triisopropylphosphine was added. The results were as follows.
EG: 9.9 mol/g atom Rh.hr
MeOH: 5.9 mol/g atom Rh.hr

EXAMPLES 2 to 6 and COMPARATIVE EXAMPLE 2

Into the same reactor as used in Example 1, 0.075 mmol of $Rh_4(CO)_{12}$, triisopropylphosphine in an amount as specified in Table 1, and 7.5 ml of N-methylpyrrolidinone, were fed, and a gas mixture of equal volumes of carbon monoxide and hydrogen was introduced to a level of about 300 kg/cm² at room temperature. Then, the reaction was conducted at 240° C. for 3 hours under a pressure condition as identified in Table 1.

The results are shown in Table 1.

TABLE 1

| | P(i-Pr)$_3$ (mmol) | P/Rh | Pressure (kg/cm$^2$) | Products EG (mol/g atom Rh.hr) | Products MeOH (mol/g atom Rh.hr) |
|---|---|---|---|---|---|
| Comparative Example 2 | 0 | 0 | 450–405 | 3.6 | 7.1 |
| Example 2 | 0.1 | 0.3 | 450–405 | 5.3 | 3.8 |
| Example 3 | 0.3 | 1.0 | 450–405 | 4.9 | 7.4 |
| Example 4 | 0.6 | 2.0 | 445–390 | 3.6 | 10.1 |
| Example 5 | 1.0 | 3.3 | 450–370 | 2.8 | 13.8 |
| Example 6 | 10.0 | 33.3 | 450–415 | 3.9 | 7.6 |

EXAMPLES 7 to 10 and COMPARATIVE EXAMPLE 3

Into the same reactor as used in Example 1, 0.075 mmol of Rh$_4$(CO)$_{12}$, a phosphine in an amount as specified in Table 2, and 7.5 ml of N-methylpyrrolidinone, were fed, and a gas mixture of equal volumes of carbon monoxide and hydrogen was filled. Then, the reaction was conducted at 220° C. for 3 hours under a reaction pressure as identified in Table 2.

The results are shown in Table 2.

TABLE 2

| | Phosphine | mmol | P/Rh | Pressure (kg/cm$^2$) | Products EG (mol/g atom Rh.hr) | Products MeOH (mol/g atom Rh.hr) |
|---|---|---|---|---|---|---|
| Example 7 | P(i-Pr)$_3$ | 0.3 | 1.0 | 450–400 | 6.1 | 4.3 |
| Example 8 | P(t-Bu)$_3$ | 0.3 | 1.0 | 450–440 | 3.4 | 0.93 |
| Example 9 | P(s-Bu)$_3$ | 0.3 | 1.0 | 440–400 | 3.8 | 8.3 |
| Example 10 | P(c-C$_6$H$_{11}$)$_3$ | 0.3 | 1.0 | 450–410 | 3.7 | 3.1 |
| Comparative Example 3 | Nil | 0 | 0 | 450–430 | 1.5 | 4.2 |

EXAMPLE 11

In the same reactor as used in Example 1, 0.075 mmol of Rh$_4$(CO)$_{12}$, 0.3 mmol of triisopropylphosphine and 7.5 ml of GBL as a solvent, were fed, and the reaction was conducted at 240° C. for 3 hours in the same manner as in Example 1. The reaction pressure changed from 450 kg/cm$^2$ to 390 kg/cm$^2$.

The results of the analysis of the reaction solution were as follows.

EG: 1.2 mol/g atom Rh.hr
MeOH: 5.0 mol/g atom Rh.hr

Further, no precipitation of catalyst was observed in the reaction solution.

COMPARATIVE EXAMPLE 4

The experiment was conducted in the same manner as in Example 11 except that no triisopropylphosphine was added. The results of the analysis of the reaction solution were as follows.

EG: 0.0 mol/g atom Rh.hr
MeOH: 0.5 mol/g atom Rh.hr

In the reaction solution, the catalyst precipitated in a substantial amount.

EXAMPLE 12

Into a Hastelloy C autoclave having an internal capacity of 35 ml, acetylacetonatobis(carbonyl)rhodium [Rh(CO)$_2$acac] containing 0.1 mg atom of rhodium, 0.5 mmol of tri-n-butylphosphine and 10 ml of DMI, were fed, and a gas mixture of equal volumes of carbon monoxide and hydrogen was introduced to 300 kg/cm$^2$ at room temperature. The autoclave was heated to 240° C., whereby the initial value of the reaction pressure was 480 kg/cm$^2$. The reaction was continued under the same condition for 2 hours. Then, the autoclave was cooled, and the reaction mixture was taken out and analyzed by gas chromatography, whereby it was found that the turnover of EG was 0.42 mol/g atom Rh.hr and that of MeOH was 27.8 mol/g atom Rh.hr.

COMPARATIVE EXAMPLE 5 and EXAMPLES 13 to 20

The experiments were conducted in the same manner as in Example 12 except that the amounts of rhodium, tri-n-butylphosphine and DMI, and the reaction conditions were changed as shown in Table 3. The results are shown in Table 3.

TABLE 3

| | Rh, (mmol) | P(n-Bu)$_3$ (mmol) | P/Rh | DMI (ml) | Temp. (°C.) | Time (hr) | Products EG (mol/g atom Rh.hr) | Products MeOH (mol/g atom Rh.hr) |
|---|---|---|---|---|---|---|---|---|
| Comparative Example 5 | 0.1 | 0 | 0 | 10 | 240 | 2 | 12.3 | 8.6 |
| Example 13 | 0.1 | 0.5 | 5 | 10 | 240 | 2 | 0.4 | 27.8 |
| Example 14 | 0.1 | 1.0 | 10 | 10 | 240 | 2 | 2.3 | 52.9 |
| Example 15 | 0.1 | 2.0 | 20 | 10 | 240 | 2 | 6.0 | 69.6 |
| Example 16 | 0.1 | 4.0 | 40 | 10 | 240 | 2 | 11.1 | 89.9 |
| Example 17 | 0.1 | 8.0 | 80 | 10 | 240 | 2 | 9.5 | 99.6 |
| Example 18 | 0.1 | 20.0 | 200 | 5 | 240 | 2 | 2.4 | 59.4 |
| Example 19 | 0.05 | 2.0 | 40 | 10 | 260 | 1 | 14.5 | 229.6 |
| Example 20 | 0.05 | 4.0 | 80 | 10 | 260 | 1 | 23.0 | 265.8 |

EXAMPLES 21 and 22

The experiments were conducted in the same manner as in Example 12 except that tricyclohexylphosphine was used instead of tri-n-butylphosphine. The results are shown in Table 4.

TABLE 4

| | Rh (mmol) | P(c-C$_6$H$_{11}$)$_3$ (mmol) | P/Rh | Products EG (mol/g atom Rh.hr) | Products MeOH (mol/g atom Rh.hr) |
|---|---|---|---|---|---|
| Example 21 | 0.1 | 0.5 | 5 | 9.3 | 34.4 |
| Example 22 | 0.1 | 1.0 | 10 | 8.0 | 25.4 |

EXAMPLES 23 and 24, and COMPARATIVE EXAMPLES 6 and 7

The experiments were conducted in the same manner as Example 13 except that tricyclopentylphosphine in an amount specified in Table 5 was used instead of tri-n-butylphosphine, NMP or DMI was used as the solvent, and the reaction was conducted at 230° C. for 2 hours. The results are shown in Table 5.

TABLE 5

| | Rh (mmol) | P(c-C$_5$H$_9$)$_3$ | P/Rh | Solvent (10 ml) | Products EG (mol/g atom Rh.hr) | MeOH (mol/g atom Rh.hr) |
|---|---|---|---|---|---|---|
| Example 23 | 0.1 | 0.1 | 1 | NMP | 20.5 | 14.9 |
| Comparative Example 6 | 0.1 | 0 | 0 | NMP | 7.1 | 5.8 |
| Example 24 | 0.1 | 0.1 | 1 | DMI | 18.5 | 29.3 |
| Comparative Example 7 | 0.1 | 0 | 0 | DMI | 6.8 | 4.2 |

EXAMPLES 25 and 26

The experiments were conducted in the same manner as in Example 13 except that 16 mmol and 25 mmol of tri-n-propylphosphine was used instead of tri-n-butylphosphine, as the trialkylphosphine. The results are shown in Table 6.

TABLE 6

| | Rh, (mmol) | P(n-Pr)$_3$ | P/Rh | DMI (ml) | Temp (°C.) | Time (hr) | Products EG (mol/g atom Rh.hr) | MeOH (mol/g atom Rh.hr) |
|---|---|---|---|---|---|---|---|---|
| Example 25 | 0.1 | 16.0 | 160 | 10 | 240 | 2 | 17.5 | 111 |
| Example 26 | 0.1 | 25.0 | 250 | 10 | 240 | 2 | 13.5 | 138 |

EXAMPLE 27

Into a Hastelloy C autoclave having an internal capacity of 35 cc, acetylacetonatobis(carbonyl)rhodium [Rh(CO)$_2$(acac)] containng 0.1 mmol of rhodium, 0.1 mmol of di(t-butyl)-n-butylphosphine and 10 ml of N-methylpyrrolidinone, were fed, and a gas mixture of equal volumes of carbon monoxide and hydrogen was introduced to 300 kg/cm$^2$ at room temperature. The autoclave was heated to 240° C. whereby the initial value of the reaction pressure was 485 kg/cm$^2$. The reaction was continued for 2 hours under the same condition. Then, the autoclave was cooled, and the reaction mixture was taken out and analyzed by gas chromatography, whereby it was found that 22.3 mol/g atom Rh.hr of ethylene glycol and 10.8 mol/g atom Rh.hr of methanol formed.

EXAMPLE 28

The reaction was conducted in the same manner as in Example 27 except that N,N'-dimethylimidazolidinone was used instead of N-methylpyrrolidinone, as the solvent, whereby it was found that 20.6 mol/g atom Rh.hr of ethylene glycol and 13.4 mol/g atom Rh.hr of methanol formed.

EXAMPLES 29 and 30

The reactions were conducted in the same manner as in Example 28 except that the amount of di(t-butyl)-n-butylphosphine was changed as shown in Table 7. The results are shown in Table 7.

TABLE 7

| | Amount of P(t-Bu)$_2$(n-Bu) (mmol) | Products (mol/g atom Rh.hr) Ethylene glycol | Methanol |
|---|---|---|---|
| Example 29 | 0.05 | 13.04 | 9.68 |
| Example 30 | 0.5 | 18.55 | 30.10 |

EXAMPLES 31 to 33

The reactions were conducted in the same manner as in Example 28 except that the phosphines identified in Table 8 were used instead of di(t-butyl)-n-butylphosphine, and the reaction temperature and the amount of the phosphine were changed as shown in Table 8. the results are shown in Table 8.

TABLE 8

| | Phosphine Type | Amount (mmol) | Reaction temperature (°C.) | Products (mol/g-atom Rh.hr) Ethylene glycol | Methanol |
|---|---|---|---|---|---|
| Example 31 | P(n-Bu)$_2$(t-Bu) | 0.1 | 230 | 11.07 | 16.58 |
| Example 32 | P(n-Bu)$_2$(t-Bu) | 0.2 | 230 | 8.80 | 19.05 |
| Example 33 | P(c-C$_6$H$_{11}$)$_2$(n-Bu) | 0.05 | 220 | 4.67 | 20.29 |

EXAMPLES 34 and 35

The reactions were conducted in the same manner as in Example 27 except that the phosphines identified in Table 9 were used instead of di(t-butyl)-n-butylphosphine, and the reaction temperature was changed to 230° C. The results are shown in Table 9.

TABLE 9

| | Phosphine | Products (mol/g-atom Rh.hr) Ethylene glycol | Methanol |
|---|---|---|---|
| Example 34 | P(i-Pr)$_2$(n-Bu) | 8.12 | 8.70 |
| Example 35 | P(t-Bu)$_2$Et | 8.62 | 3.80 |

COMPARATIVE EXAMPLE 8

The reaction was conducted in the same manner in Example 27 except that the reaction temperature was changed to 230° C. without using di(t-butyl)-n-butylphosphine, whereby it was found that 7.63 mol/g atom Rh.hr of ethylene glycol and 5.78 mol/g atom Rh.hr of methanol formed.

EXAMPLE 36

Into a Hastelloy C autoclave having an internal capacity of 35 cc, acetylacetonatobis(carbonyl)rhodium [Rh(CO)$_2$(acac)] containing 0.6 mmol of rhodium, 0.6 mmol of di(t-butyl)-n-butylphosphine and 4 ml of N,N'-dimethylimidazolidinone, were fed and a gas mixture of equal volumes of carbon monoxide and hydrogen was introduced to 300 kg/cm$^2$ at room temperature. The autoclave was heated to 230° C., whereby the initial value of the reaction pressure was 480 kg/cm$^2$. A gas mixture of equal volumes of carbon monoxide and hydrogen was supplemented to a pressure of 520 kg/cm$^2$, and the reaction was initiated. The gas was supplemented when the pressure dropped to 500 kg/cm$^2$, thereby to return the pressure to 520 kg/cm$^2$. While this operation was repeated, the reaction was continued for 1 hour. Then, autoclave was cooled, and the reaction mixture was taken out and analyzed by gas chromatography, whereby it was found that the turn-over of ethylene glycol was 12.85 mol/g atom Rh.hr and that of methanol was 19.21 mol/g atom Rh.hr. The space time yield of ethylene glycol reached to a level of 120 g/l.hr based on the feed solvent. [In the typical conventional rhodium catalyst system of rhodium/cesium benzoate/N-methylmorpholine/sulforane (solvent), the space time yield of ethylene glycol is as low as 118 g/l.hr even when a high pressure of 1030 kg/cm$^2$ and a high temperature of 260° C. were used as reaction conditions. (José, L, Vidal, and W. E. Walker, Inorganic Chemistry, Vol. 19, page 896)]

EXAMPLE 37

The reaction was conducted in the same manner as in Example 36 except that the amount of rhodium was changed to 0.9 mmol, and the amount of di(t-butyl)-n-butylphosphine was changed to 0.9 mmol, whereby it was found that 9.39 mol/g atom Rh.hr of ethylene glycol and 19.98 mol/g atom Rh.hr of methanol formed. The space time yield of ethylene glycol reached 130 g/l.hr based on the feed solvent.

EXAMPLE 38

Into a Hastelloy C autoclave having an internal capacity of 35 cc, acetylacetonatobis(carbonyl)rhodium [Rh(CO)$_2$(acac)] containing 0.1 mg atom of rhodium, 0.1 mmol of tri-iso-propylphosphine, 0.5 mmol of tetrakis(dimethylamino)ethylene and 10 ml of N,N'-dimethylimidazolidinone, were fed, and a gas mixture of equal volumes of carbon monoxide and hydrogen was introduced to 300 kg/cm$^2$ at room temperature. The autoclave was heated to 240° C., whereby the initial value of the reaction pressure was 480 kg/cm$^2$. The reaction was continued for 2 hours under the same condition. Then, the autoclave was cooled, and the reaction mixture was taken out and analyzed by gas chromatography, whereby it was found that 17.72 mol/g atom Rh.hr of ethylene glycol and 16.07 mol/g atom Rh.hr of methanol formed.

EXAMPLES 39 to 43

The reactions were conducted in the same manner as in Example 38 except that the amine compounds identified in Table 10 were added in the respective amounts identified in Table 10, instead of tetrakis(dimethylamino)ethylene. The results are shown in Table 10.

TABLE 10

| | Amine compound | | Products (mol/g atom Rh.hr) | |
|---|---|---|---|---|
| | Type | Amount (mmol) | Ethylene glycol | Methanol |
| Example 39 | 4-Dimethylaminopyridine | 0.02 | 18.90 | 21.17 |
| Example 40 | 4-Dimethylaminopyridine | 0.05 | 16.76 | 19.04 |
| Example 41 | 1-methylimidazole | 1.5 | 16.27 | 14.19 |
| Example 42 | 1-methylimidazole | 5.0 | 18.44 | 12.46 |
| Example 43 | Nil | 0.0 | 14.26 | 18.73 |

EXAMPLE 44

Into a Hastelloy C autoclave having internal capacity of 35 cc, acetylacetonatobis(carbonyl)rhodium [Rh(CO)$_2$(acac)] containing 0.4 mg atom of rhodium, 0.4 mmol of tri-iso-propylphosphine, 6.0 mmol of 1-methylimidazole and 4 ml of N,N'-dimethylimidazolidinone, were fed, and a gas mixture of equal volumes of carbon monoxide and hydrogen was introduced to 300 kg/cm$^2$ at room temperature. The autoclave was heated to 250° C., whereby the initial value of the reaction pressure was 490 kg/cm$^2$. Further, a gas mixture of equal volumes of carbon monoxide and hydrogen was supplemented to 520 kg/cm$^2$, and then reaction was initiated. When the pressure dropped to 500 kg/cm$^2$, the gas was supplemented to return the pressure to 520 kg/cm$^2$, and while repeating this operation, reaction was continued for 1 hour. Then, autoclave was cooled, and the reaction mixture was taken out and analyzed by gas chromatography, whereby it was found that 18.68 mol/g atom Rh.hr of ethylene glycol and 18.00 mol/g atom Rh.hr of methanol formed.

EXAMPLES 45 to 54 and COMPARATIVE EXAMPLE 9

The reactions were conducted in the same manner as in Example 44 except that the amounts of rhodium, triisopropylphosphine and 1-methylimidazole were changed, and reaction temperature was varied as shown in Table 11. The results are shown in Table 11.

TABLE 11

| | Rh(CO)$_2$(acac) (mg-atom Rh) | P(i-Pr)$_3$ (mmol) | 1-Methylimidazole (mmol) | Reaction temp. (°C.) | Products | | Methanol (mol/g atom Rh.hr) |
|---|---|---|---|---|---|---|---|
| | | | | | Ethylene glycol | | |
| | | | | | Amount (mol/g atom Rh.hr) | Space time yield (g/l.hr) | |
| Example 45 | 0.4 | 0.2 | 6.0 | 240 | 17.48 | 108 | 13.53 |
| Example 46 | 0.4 | 0.8 | 4.0 | 240 | 18.33 | 114 | 11.98 |
| Example 47 | 0.4 | 0.4 | 4.0 | 240 | 30.75 | 191 | 21.20 |
| Example 48 | 0.4 | 0.4 | 4.0 | 230 | 26.18 | 162 | 18.55 |
| Example 49 | 0.6 | 0.6 | 6.0 | 235 | 20.67 | 192 | 12.60 |
| Example 50 | 0.6 | 0.6 | 6.0 | 230 | 25.0 | 233 | 12.80 |
| Example 51 | 0.6 | 0.6 | 6.0 | 225 | 19.35 | 180 | 8.93 |
| Example 52 | 0.6 | 0.6 | 6.0 | 220 | 17.60 | 164 | 6.45 |
| Example 53 | 0.9 | 0.9 | 6.0 | 230 | 19.51 | 272 | 12.83 |
| Example 54 | 0.9 | 0.9 | 4.5 | 230 | 20.11 | 281 | 12.89 |
| Comparative Example 9 | 0.4 | 0.0 | 6.0 | 240 | 7.68 | — | 18.17 |

EXAMPLES 55 to 59

The reactions were conducted in the same manner as in Example 44 except that the trialkylphosphines identified in Table 12 were added in the respective amounts identified in Table 12, instead of tri-iso-propylphosphine, and the amounts of rhodium and 1-methylimidazole were changed as shown in Table 12. The results are shown in Table 12.

TABLE 12

| | Rh(CO)₂ (acac) (mg-atom Rh) | Trialkylphosphine Type | Trialkylphosphine Amount (mmol) | 1-Methyl imidazole (mmol) | Reaction temp. (°C.) | Products Ethylene glycol Amounts (mol/g atom Rh.hr) | Products Ethylene glycol Space time yield (g/l.hr) | Methanol (mol/g atom Rh.hr) |
|---|---|---|---|---|---|---|---|---|
| Example 55 | 0.6 | P(c-C₅H₉)₃ | 0.6 | 6.0 | 230 | 22.38 | 208 | 16.02 |
| Example 56 | 0.6 | " | 0.6 | 3.0 | 230 | 22.98 | 214 | 15.7 |
| Example 57 | 0.6 | " | 0.3 | 6.0 | 230 | 16.25 | 151 | 8.22 |
| Example 58 | 0.6 | P(t-Bu)₂(n-Bu) | 0.6 | 0.6 | 230 | 16.39 | 153 | 10.14 |
| Example 59 | 0.9 | " | 0.9 | 4.5 | 230 | 19.80 | 276 | 13.15 |

EXAMPLES 60 to 64

The reactions were conducted in the same manner as in Example 38 except that the amine compounds identified in Table 13 were added in the respective amounts identified in Table 13, instead of 0.5 mmol of tetrakis(-dimethylamino)ethylene, and tetraglyme was employed instead of N,N'-dimethylimidazolidinone. The results are shown in Table 13.

TABLE 13

| | Amine compound Type | Amount (mmol) | Products (mol/g atom Rh.hr) Ethylene glycol | Methanol |
|---|---|---|---|---|
| Example 60 | Tetrakis(dimethyl-amino)ethylene | 0.05 | 8.3 | 25.2 |
| Example 61 | 4-Dimethylamino-pyridine | 0.1 | 10.15 | 16.4 |
| Example 62 | 1-Methylimidazole | 0.4 | 15.95 | 17.35 |
| Example 63 | 1-Methylimidazole | 5.0 | 16.45 | 19.40 |
| Example 64 | Nil | 0.0 | 0.0 | 22.05 |

EXAMPLE 65

The reaction was conducted in the same manner as in Example 38 except that 4.0 mmol of tri-n-butylphosphine was used instead of 0.1 mmol of tri-iso-propylphosphine, and 0.5 mmol of 1-methylimidazole was used instead of 0.5 mmol of tetrakis(dimethylamino)ethylene, whereby it was found that 1.95 mol/g atom Rh.hr of ethylene glycol and 44.70 mol/g atom Rh.hr of methanol formed.

EXAMPLE 66

The reaction was conducted in the same manner as in Example 38 except that 0.1 mmol of tricyclopentylphosphine was used instead of 0.1 mmol of tri-isopropylphosphine, and 1.0 mmol of 1-methylimidazole was used instead of 0.5 mmol of tetrakis(dimethylamino)ethylene, whereby it was found that 22.25 mol/g atom Rh.hr of ethylene glycol and 20.20 mol/g atom Rh.hr of methanol formed.

EXAMPLES 67 and 68

The reactions were conducted in the same manner as in Example 50 except that the amount of 1-methylimidazole was changed as shown in Table 14 and tetraglyme was used instead of N,N'-dimethylimidazolidinone. The results are shown in Table 14.

TABLE 14

| | 1-Methylimidazole (mmol) | Products (mol/g atom Rh.hr) Ethylene glycol | Methanol |
|---|---|---|---|
| Example 67 | 3.0 | 19.49 | 20.0 |
| Example 68 | 6.0 | 17.75 | 16.90 |

EXAMPLES 69 to 71 COMPARATIVE EXAMPLE 10

The reactions were conducted in the same manner as in Example 38 except that the amine compounds identified in Table 15 were added in the respective amounts identified in Table 15, instead of tetrakis(dimethylamino)ethylene, and N-methylpyrrolidinone was used instead of N,N'-dimethylimidazolidinone. The results are shown in Table 15.

TABLE 15

| | Amine compound Type | Amount (mmol) | Products (mol/g atom Rh.hr) Ethylene glycol | Methanol |
|---|---|---|---|---|
| Example 69 | 4-Dimethylamino-pyridine | 0.5 | 21.75 | 16.7 |
| Example 70 | 1-Methylimidazole | 0.5 | 23.05 | 12.65 |
| Example 71 | Nil | 0.0 | 13.78 | 11.55 |
| Comparative* Example 10 | 1-Methylimidazole | 0.5 | 10.45 | 9.15 |

*Tri-iso-propyl phosphine was not added.

EXAMPLES 72 to 78

The reactions were conducted in the same manner as in Example 44 except that the amount of rhodium was changed to 0.6 mg atom Rh, the amounts of the trialkylphosphine and the amine compound were changed as shown in Table 16, N-methylpyrrolidinone was used instead of N,N′-dimethylimidazolidinone, and the reaction temperature was changed to 230° C. The results are shown in Table 16.

TABLE 16

| | Trialkylphosphine | | Amine compound | | Products | | |
|---|---|---|---|---|---|---|---|
| | | | | | Ethylene glycol | | Methanol |
| | Type | Amount (mmol) | Type | Amount (mmol) | Amount (mol/g atom Rh.hr) | Space time yield (g/l.hr) | (mol/g atom Rh.hr) |
| Example 72 | P(i-Pr)$_3$ | 0.6 | 1-Methylimidazole | 10.0 | 18.37 | 171 | 8.11 |
| Example 73 | P(i-Pr)$_3$ | 0.6 | 1-Methylimidazole | 6.3 | 19.98 | 180 | 10.5 |
| Example 74 | P(i-Pr)$_3$ | 0.6 | 1-Methylimidazole | 3.0 | 17.72 | 165 | 10.3 |
| Example 75 | P(i-Pr)$_3$ | 0.6 | 4-Dimethylamino-pyridine | 3.0 | 14.18 | 132 | 7.38 |
| Example 76 | P(i-Pr)$_3$ | 0.6 | 4-Dimethylamino-pyridine | 0.3 | 17.73 | 165 | 13.26 |
| Example 77 | P(c-C$_5$H$_9$)$_3$ | 0.6 | 1-Methylimidazole | 6.0 | 16.84 | 157 | 10.38 |
| Example 78 | P(c-C$_5$H$_9$)$_3$ | 0.6 | Nil | 0.0 | 11.22 | 105 | 27.47 |

EXAMPLE 79

The interior of a shaking-type Hastelloy C autoclave having an internal capacity of 30 ml was flushed with nitrogen, and then tetrarhodium dodecacarbonyl[Rh$_4$(CO)$_{12}$] containing 0.3 mg atom of rhodium, 0.3 mmol of triisopropylphosphine, 0.3 mmol of N-methylpiperidine and 7.5 ml of N-methylpyrrolidinone as a solvent, were fed. The mixture was thoroughly mixed, and then the autoclave was closed. The interior of the autoclave was flushed with a gas mixture of equal volumes of carbon monoxide and hydrogen, and the same gas was introduced to a pressure of 400 kg/cm$^2$. The reaction was conducted at 240° C. for 2 hours while shaking the autoclave. The reaction pressure changed from 510 kg/cm$^2$ to 450 kg/cm$^2$. After the completion of the reaction, the autoclave was cooled to room temperature, and the internal pressure was brought to normal pressure by slowly releasing the major portion of the gas. Then, the reaction mixture was taken out, and analyzed by gas chromatography, whereby it was found that 9.14 mol/g atom Rh.hr of ethylene glycol and 10.78 mol/g atom Rh.hr of methanol formed.

EXAMPLES 80 to 93

The reactions were conducted in the same manner as in Example 79 except that the amine compounds identified in Table 17 were added in the respective amounts identified in Table 17, instead of N-methylpiperidine. The results are shown in Table 17.

TABLE 17

| | Amine compound | | Products (mol/g atom Rh.hr) | |
|---|---|---|---|---|
| | Type | Amount (mmol) | Ethylene glycol | Methanol |
| Example 80 | N—Methylpiperidine | 1.0 | 11.38 | 9.53 |
| Example 81 | N—Methylpiperidine | 3.0 | 11.34 | 7.65 |
| Example 82 | N—Methylpiperidine | 10.0 | 11.37 | 7.11 |
| Example 83 | 1-Ethylimidazole | 1.0 | 16.09 | 14.25 |
| Example 84 | Imidazole | 1.0 | 15.42 | 13.77 |
| Example 85 | 1-Methylbenz-imidazole | 1.0 | 9.21 | 18.62 |
| Example 86 | Benzimidazole | 1.0 | 8.70 | 13.49 |
| Example 87 | 4-Dimethylamino-pyridine | 1.0 | 14.61 | 8.81 |
| Example 88 | Pyridine | 1.0 | 9.44 | 14.83 |
| Example 89 | 2-Hydroxypyridine | 1.0 | 10.53 | 13.74 |
| Example 90 | Triethylamine | 1.0 | 14.05 | 12.93 |
| Example 91 | Morpholine | 1.0 | 10.24 | 17.32 |
| Example 92 | Aniline | 1.0 | 11.03 | 17.80 |
| Example 93 | Nil | 0.0 | 7.54 | 9.75 |

EXAMPLES 94 to 96

The reactions were conducted in the same manner as in Example 79 except that the amine compounds identified in Table 18 were added in the respective amounts identified in Table 18, instead of using 0.3 mmol of N-methylpiperidine, the amount of N-methylpyrrolidinone was changed to 3.75 ml, and the reaction time was changed to 1 hour. The results are shown in Table 18.

TABLE 18

| | Amine compound | | Products | | |
|---|---|---|---|---|---|
| | | | Ethylene glycol | | Methanol |
| | Type | Amount (mmol) | Amount (mol/g atom Rh.hr) | Space time yield (g/l.hr) | (mol/g atom Rh.hr) |
| Example 94 | N—methyl-piperidine | 1.0 | 20.47 | 102 | 13.39 |
| Example 95 | 4-Dimethyl-amino-pyridine | 1.0 | 17.80 | 88 | 9.74 |
| Example 96 | 1-Ethyl-imidazole | 1.0 | 23.53 | 116 | 15.73 |

EXAMPLE 97

The reaction was conducted in the same manner as in Example 79 except that the reaction temperature was changed to 220° C., and γ-butyrolactone was used instead of N-methylpyrrolidinone, whereby it was found that 6.07 mol/g atom Rh.hr of ethylene glycol, 5.82 mol/g atom Rh.hr of methanol and 0.4 mol/g atom Rh.hr of methyl formate formed.

COMPARATIVE EXAMPLE 11

The reaction was conducted in the same manner as in Example 97 except that no triisopropylphosphine was added, whereby it was confirmed that 1.95 mol/g atom Rh.hr of ethylene glycol, 2.40 mol/g atom Rh.hr of methanol and 0.05 mol/g atom Rh.hr of methyl formate formed.

EXAMPLES 98 and 99 and COMPARATIVE EXAMPLE 12

The reactions were conducted in the same manner as in Example 38 except that tri-n-butylphosphine was added in the amounts identified in Table 19, instead of 0.1 mmol of tri-iso-propylphosphine, and 10 ml of 1-methylimidazole was used instead of tetrakis(dimethylamino)ethylene and N,N'-dimethylimidazolidinone. The results are shown in Table 19.

TABLE 19

| | Trialkylphosphine | | Products (mol/g atom Rh.hr) | |
|---|---|---|---|---|
| | Type | Amount (mmol) | Ethylene glycol | Methanol |
| Example 98 | Tri-n-butyl-phosphine | 0.1 | 1.35 | 1.5 |
| Example 99 | Tri-n-butyl phosphine | 5.0 | 4.63 | 34.10 |
| Comparative Example 12 | Nil | 0.0 | 0.0 | 0.0 |

EXAMPLES 100 and 101

The reactions were conducted in the same manner as in Example 70 except that the trialkylphosphines identified in Table 20 were used in an amount of 0.1 mmol, instead of 0.6 mmol of tri-iso-propylphosphine. The results are shown in Table 20.

TABLE 20

| | Trialkylphosphine | Products (mol/g atom Rh.hr) | |
|---|---|---|---|
| | | Ethylene glycol | Methanol |
| Example 100 | $P(t-Bu)_3$ | 13.46 | 6.07 |
| Example 101 | $P(c-C_6H_{11})_3$ | 18.10 | 16.56 |

EXAMPLE 102

Into the same autoclave as used in Example 79, 0.075 mmol of $Rh_4(CO)_{12}$, 0.05 mmol of cesium acetate, 1.00 mmol of 2-hydroxypyridine, 0.30 mmol of tri-iso-propylphosphine and 7.5 ml of tetraglyme as a solvent, were fed, and reacted at 220° C. for 2 hours in the same manner as in Example 79. The reaction pressure changed from 450 kg/cm$^2$ to 430 kg/cm$^2$. The results of the analysis of the reaction solution were as follows.
EG: 4.25 mol/g atom Rh.hr
MeOH: 4.43 mol/g atom Rh.hr
In the reaction solution, no precipitation of e.g. catalyst was observed.

COMPARATIVE EXAMPLE 13

The reaction was conducted in the same manner as in Example 102 except that no tri-iso-propylphosphine was added. The reaction pressure was 450 kg/cm$^2$.
The results of the analysis of the reaction solution were as follows:
EG: 1.08 mol/g atom Rh.hr
MeOH: 1.53 mol/g atom Rh.hr
In the reaction solution, a small amount of the precipitate of catalyst was observed.

EXAMPLE 103

The interior of a Hastelloy C autoclave having an internal capacity of 30 cc, was flushed with nitrogen, and then 0.025 mmol of tetrarhodium dodecacarbonyl $[Rh_4(CO)_{12}]$, 0.033 mmol of triruthenium dodecacarbonyl $[Ru_3(CO)_{12}]$, 0.4 mmol of triisopropylphosphine, 1.0 mmol of 4-N,N-dimethylaminopyridine and 7.5 ml of N-methylpyrrolidinone as a solvent, were fed, and a gas mixture of equal volumes of carbon monoxide and hydrogen was introduced to 350 kg/cm$^2$ at room temperature. The autoclave was heated to a temperature of 240° C., and the reaction was continued for 2 hours under the same condition. The reaction pressure was 500 kg/cm$^2$ After the completion of the reaction, the autoclave was cooled to room temperature, and the internal pressure was brought to normal pressure by slowly releasing the major portion of the gas. The reaction mixture was taken out, and the products were analyzed by gas chromatography, whereby it was found that 24.9 mol/g atom Rh.hr of ethylene glycol and 15.0 mol/g atom Rh.hr of methanol formed.

COMPARATIVE EXAMPLE 14

The experiment was conducted in the same manner as in Example 103 except that no triisopropylphosphine and no 4-N,N-dimethylaminopyridine were added. The results are shown below.
EG: 1.1 mol/g atom Rh.hr
MeOH: 1.3 mol/g atom Rh.hr

EXAMPLES 104 to 106

The experiments were conducted in the same manner as in Example 103 by using the same reactor as used in Example 103 under the feeding and reaction conditions as identified in Table 21. The results as shown in Table 21 were obtained. In each case, no precipitation of metal of the catalyst was observed.

TABLE 21

| Example | Rh*[1] (mg atom) | Ru*[2] (mg atom) | First additive (mmol) | Second additive (mmol) | Solvent | Temp. (°C.) | Pressure*[3] (kg/cm$^2$) | Time (hr) | Products (mol/g atom Rh.hr) | |
|---|---|---|---|---|---|---|---|---|---|---|
| | | | | | | | | | EG | MeOH |
| 104 | 0.1 | 0.1 | $P(i-Pr)_3$ (0.2) | 2-Methyl-imidazole (10) | Toluene | 240 | 500 | 2 | 18.1 | 30.8 |
| 105 | 0.1 | 0.1 | $P(i-Pr)_3$ (0.4) | 2-Methyl-imidazole (10) | DMI | 260 | 500 | 2 | 21.3 | 10.5 |
| 106 | 0.1 | 0.1 | $P(i-Pr)_3$ (0.2) | Nil | NMP | 240 | 645 | 2 | 25.2 | 32.9 |

*[1]Rh: $Rh_4(CO)_{12}$
*[2]Ru: $Ru_3(CO)_{12}$
*[3]In Examples 104–106, the CO/H$_2$ ratio was 1.

EXAMPLES 107 to 110

The reactions were conducted in the same manner as in Example 103 by feeding into the same reactor as used in Example 103, 0.025 mmol of $Rh_4(CO)_{12}$, 0.033 mmol of $Ru_3(CO)_{12}$, a phosphine as identified in Table 22 and 0.2 mmol of 4-N,N-dimethylaminopyridine, whereby the results as shown in Table 22 were obtained.

TABLE 22

| Example | Type of phosphine | Amount of phosphine (mmol) | Products (mol/g atom Rh.hr) | |
|---|---|---|---|---|
| | | | EG | MeOH |
| 107*[1] | $P(i-Pr)_3$ | 0.6 | 19.6 | 22.5 |
| 108*[2] | $P(c-C_6H_{11})_3$ | 0.4 | 22.3 | 20.7 |
| 109 | $P(t-Bu)_3$ | 0.4 | 8.1 | 4.6 |
| 110 | $P(n-Bu)_3$ | 1.0 | 6.6 | 39.2 |

*[1] $CO/H_2$ ratio = 1
*[2] $CO/H_2$ ratio = ½

EXAMPLES 111 to 119

The reactions were conducted in the same manner as in Example 103 by feeding into the same reactor as used in Example 103, 0.025 mmol of $Rh_4(CO)_{12}$, 0.033 mmol of $Ru_3(CO)_{12}$, 0.2 mmol of $P(i-Pr)_3$ and 0.2 mmol of an amine as identified in Table 23, whereby the results as shown in Table 23 were obtained.

TABLE 23

| Example | Type of amine | Products (mol/g atom Rh.hr) | |
|---|---|---|---|
| | | EG | MeOH |
| 111 | Imidazole | 17.6 | 11.8 |
| 112 | N—ethylimidazole | 17.7 | 12.2 |
| 113 | Benzimidazole | 18.3 | 16.1 |
| 114 | 4-N,N—dimethylaminopyridine | 19.0 | 12.8 |
| 115 | N—methylbenzimidazole | 16.3 | 17.0 |
| 116 | 2-Hydroxypyridine | 17.4 | 16.8 |
| 117 | Pyridine | 16.4 | 18.8 |
| 118 | N—methylpiperidine | 17.3 | 12.6 |
| 119 | N—methylpyrrolidine | 17.6 | 17.3 |

EXAMPLES 120 to 129

The reactions were conducted in the same manner as in Example 103 by feeding into the same reactor as used in Example 103, 0.025 mmol of $Rh_4(CO)_{12}$, 0.033 mmol of $Ru_3(CO)_{12}$ and a phosphine and 7.5 ml of a solvent as identified in Table 24, whereby the results as shown in Table 24 were obtained.

TABLE 24

| Example | Type of phosphine | Amount of phosphine (mmol) | Solvent | Products (mol/g atom Rh.hr) | |
|---|---|---|---|---|---|
| | | | | EG | MeOH |
| 120 | $P(i-Pr)_3$ | 0.2 | NMP | 13.4 | 12.8 |
| 121 | $P(s-Bu)_3$ | 0.2 | NMP | 13.5 | 16.8 |
| 122 | $P(t-Bu)_3$ | 0.2 | NMP | 4.2 | 0.18 |
| 123 | $P(i-Bu)_3$ | 0.2 | NMP | 1.9 | 1.8 |
| 124 | $PEt_3$ | 0.2 | NMP | 1.8 | 3.9 |
| 125 | $P(c-C_6H_{11})_3$ | 0.2 | NMP | 13.8 | 13.4 |
| 126 | $P(i-Pr)_3$ | 0.2 | DMI | 12.5 | 19.2 |
| 127 | $P(i-Pr)_3$ | 0.2 | GBL | 4.4 | 18.2 |
| 128 | $P(n-Bu)_3$ | 2.0 | NMP | 3.3 | 49.3 |
| 129 | $P(n-Bu)_3$ | 10.0 | NMP | 5.7 | 62.5 |

EXAMPLE 130

The reaction was conducted in the same manner as in Example 103 by feeding into the same reactor as used in Example 103, 0.025 mmol of $Rh_4(CO)_{12}$, 0.067 mmol of $Ru_3(CO)_{12}$, 0.3 mmol of tri-iso-propylphosphine and 7.5 ml of N-methylpyrrolidinone, whereby 13.5 mol/g atom Rh.hr of ethylene glycol and 13.5 mol/g atom Rh.hr of methanol formed.

We claim:

1. A process for producing aliphatic alcohols by reacting carbon monoxide and hydrogen in a liquid phase in the presence of a catalyst system, comprising:
   rhodium, and a trialkylphosphine of the formula: $PR_2R_2R_3$, wherein each of $R_1$, $R_2$ and $R_3$ is a primary alkyl group, a secondary alkyl group, a tertiary alkyl group or a cycloalkyl group, as the catalyst components.

2. The process according to claim 1 wherein said trialkylphosphine component is present in the catalyst system in an amount of at least 0.2 mole per 1 g atom of rhodium.

3. The process according to claim 1, wherein, in said trialkylphosphine, $R_1$ is a primary alkyl group, $R_2$ is a secondary alkyl group, a tertiary alkyl group or a cycloalkyl group, and $R_3$ is a primary alkyl group, a secondary alkyl group, a tertiary alkyl group or a cycloalkyl group.

4. The process according to claim 1, wherein the concentration of rhodium in the reaction solution is within a range of from 0.0001 to 10 g atom per 1 liter of the reaction solution.

5. The process according to claim 1, wherein an amine compound is used as an additional catalyst component.

6. The process according to claim 5, wherein the amine compound is present in an amount of from 0.001 to 1000 mols per 1 g atom of rhodium.

7. The process according to claim 1, wherein ruthenium is present as an additional catalyst component.

8. The process according to claim 7, wherein the trialkylphosphine is present in an amount of at least 0.2 mol per 1 g atom of the sum of rhodium and ruthenium as metals.

9. The process according to claim 7, wherein the concentration of the sum of rhodium and ruthenium as metals in the reaction solution is within a range of from 0.0001 to 10 mols per 1 liter of the reaction solution.

10. The process according to claim 9, wherein the atomic ratio of ruthenium to the sum of rhodium and ruthenium as metals is within a range of from 0.1 to 0.9.

11. The process according to claim 7, wherein an amine compound is present as a further catalyst component.

12. The process according to claim 7, wherein the amine compound is present in an amount of from 0.001 to 1000 mols per 1 g atom of the sum of rhodium and ruthenium as metals.

13. The process according to claim 1, wherein the total of the carbon monoxide partial pressure and the hydrogen partial pressure in the reaction system is within a range of from 100 to 3000 $kg/cm^2$.

14. The process according to claim 1, wherein the reaction temperature in the reaction system is within a range of from 100° to 350° C.

15. The process according to claim 7, wherein, in said trialkylphosphine, group $R_1$ is a primary alkyl group, group $R_2$ is a secondary alkyl group, a tertiary alkyl group or a cycloalkyl group, and group $R_3$ is a primary alkyl group, a secondary alkyl group, a tertiary alkyl group or a cycloalkyl group.

* * * * *